United States Patent
Allen et al.

(10) Patent No.: US 8,594,942 B2
(45) Date of Patent: Nov. 26, 2013

(54) COMPUTATIONAL METHOD AND SYSTEM FOR IDENTIFYING NETWORK PATTERNS IN COMPLEX BIOLOGICAL SYSTEMS DATA

(75) Inventors: Keith D. Allen, Cary, NC (US); Marie Coffin, Cary, NC (US)

(73) Assignee: Metabolon, Inc., Durham, NC (US)

(*) Notice: Subject to any disclaimer, the term of this patent is extended or adjusted under 35 U.S.C. 154(b) by 1667 days.

(21) Appl. No.: 11/192,804

(22) Filed: Jul. 29, 2005

(65) Prior Publication Data
US 2006/0031210 A1    Feb. 9, 2006

Related U.S. Application Data

(60) Provisional application No. 60/592,745, filed on Jul. 30, 2004.

(51) Int. Cl.
G06F 19/00    (2011.01)
G06F 19/12    (2011.01)
G06G 7/58    (2006.01)

(52) U.S. Cl.
USPC ............................................. 702/19; 703/11

(58) Field of Classification Search
None
See application file for complete search history.

(56) References Cited

U.S. PATENT DOCUMENTS

| | | |
|---|---|---|
| 6,465,195 B1 | 10/2002 | Holtzman et al. |
| 6,500,633 B1 | 12/2002 | Compton et al. |
| 6,537,744 B1 | 3/2003 | Al-Bayati |
| 6,540,691 B1 | 4/2003 | Phillips |

FOREIGN PATENT DOCUMENTS

WO    WO 01/21839    *    3/2001

OTHER PUBLICATIONS

Russell et al. Artificial Intelligence: A Modern Approach, 2nd edition, Pearson Education, Inc.: Upper Saddle River, NJ, 2003, pp. 73-81.*
Blanch et al. Biochemical Engineering. New York: Marcel Dekker, Inc. 1996, pp. 60-67.*
Ogata et al. Computations with the KEGG pathway database. BioSystems, vol. 47, 1998, pp. 119-128.*
Jackson RC. Toxicity prediction from metabolic pathway modelling, Toxicology, vol. 102, 1995, pp. 197-205.*
Bogaards et al. Prediction of interindividual variation in drug plasma levels in in vivo from individual enzyme kinetic data and physiologically based pharmacokinetic modeling. European Journal of Pharmaceutical Sciences, vol. 12, 2000, pp. 117-124.*
Wilson et al., "Prediction of Coronary Heart Disease Using Risk Factor Categories," Circulation, Journal of the American Heart Association, pp. 1837-1847 (May 12, 1998).

* cited by examiner

Primary Examiner — Lori A Clow
(74) Attorney, Agent, or Firm — Jenkins, Wilson, Taylor & Hunt, P.A.

(57) ABSTRACT

The present invention is a data query and analysis tool useful for identifying patterns in experimental data. The methods and systems of the current invention provide context for biological data, including metabolic, gene expression and proteomic data, by applying the data to a network representation of biological processes. In doing so, Nodewalker moves beyond the traditional linear pathway view of biology to a network view, and uses the network as a data integration tool to seamlessly merge disparate data streams.

18 Claims, 6 Drawing Sheets
(6 of 6 Drawing Sheet(s) Filed in Color)

COMPUTATIONAL METHOD AND SYSTEM FOR IDENTIFYING NETWORK PATTERNS IN COMPLEX BIOLOGICAL SYSTEMS DATA

CROSS REFERENCE TO RELATED APPLICATION

This application claims the benefit of, and incorporates herein by reference in its entirety, U.S. Provisional Application No. 60/592,745, filed Jul. 30, 2004.

This invention was made with United States Government support under Cooperative Agreement No. 70NANB2H3009 awarded by the National Institute of Standards and Technology (NIST). The United States Government has certain rights in the invention.

FIELD OF THE INVENTION

The present invention pertains to the field of computational data analysis, and, in particular, to identification of network patterns within biological systems data.

BACKGROUND

Systems biology is an important and relatively new research field that is generating massive quantities of oftentimes disparate data. Interest in studying biology from a systems perspective has grown as the assumption of a linear relationship between gene and function has been recognized to be overly simplistic, at best. A "cause-and-effect" relationship between a single gene, its product, and a phenotype (or disease state) is the exception, not the rule. Some highly successful biopharmaceutical products, including insulin and erythropoietin, operate through their ability to modulate such linear relationships. However, problems such as ligand redundancies and cell-type specificities obfuscate the development of a pharmaceutical or agricultural product. To further complicate matters, many systems operate through nonlinear dose dependencies. In other words, at one concentration a compound may have one effect (such as an anti-inflammatory effect), while at a different concentration in the same cell type the compound may have an opposite effect (such as a pro-inflammatory effect). Issues of ligand redundancy, cell-type specificity, and nonlinear dose dependency are difficult to reconcile in a product development environment, even in cases where gene function is known or predictable. To further complicate matters, many diseases are polygenic, so not only do multiple gene products require identification, but alternate treatment compounds are likely required to address the role each gene product plays in a disease process. M. Khodadoust and T. Klein (2001) *Nature Biotech.* 19:707.

For years it was assumed that gene function was determinable by obtaining a gene sequence and performing a homology-based comparison. The central dogma is that similar sequence equals similar structure that equals similar function. Gene annotations found in public databases are far from infallible and over-reliance on them may misdirect research efforts. In many cases, only a very small percentage of any given genome is actually experimentally annotated. Homology sequence comparisons and blanket application of the central dogma supply the remaining annotation. While amino acid identity greater than 40 percent of two complete protein sequences infers structural similarity, it does not necessarily infer functional similarity. Additional sequence conservation in an active site region is required for accurate prediction of function. Wilson et al. (2000) *J. Mol. Biol.* 297:233-249. Proteins are typically organized into families based on the similarity of three-dimensional structures. In some cases, members of the same protein family may have no detectable sequence similarity, illustrating that structural similarities do not necessarily impute sequence similarities, and vice versa. Current annotation available from public sources is largely incomplete, and as a result, sequence comparison is not a viable approach to determining the relative roles of genes sequenced in genomics projects.

To meet the challenge of understanding complex biological systems, scientists require the ability to analyze complex data sets. As noted above, the sequencing of entire genomes has not led to an industry pipeline bulging with new life sciences products, nor has it led to an understanding of the function of all the sequenced genes. Currently, less than 5 percent of genes with annotation available from a public database are sufficiently well annotated for the information to be used directly in the development of products. As a result, a number of research technologies, such as gene expression profiling, metabolite analysis, phenotypic profiling, proteomics, 3-D protein structural analysis, protein expression, identification of biochemical pathways or networks, genotyping (including polymorphisms) and scientific literature tools are under development to help identify gene function. Each technology has its strengths and weaknesses but all are necessary, as no single existing technology is sufficient to identify the function of all genes.

To meet the challenge of analyzing large, complex data sets, researchers require tools that organize, analyze and present data in a meaningful way. Especially helpful are pattern recognition tools, and tools that place data in a biological context. Presented herein are computational methods and systems for identifying, from data, network patterns in complex biological systems.

SUMMARY OF THE INVENTION

The present invention provides methods and systems useful for identifying patterns in biological data. Methods and systems of the present invention are useful in creating a tool for data analysis, wherein the tool is comprised of (a) loading a reference graph from a reference data source, wherein the paths of the graph are associated with metabolic, regulatory, and signaling pathway network regions; (b) selecting at least one perturbed node to be analyzed; (c) placing the perturbed node to be analyzed at the center of a graph; (d) defining a predetermined search depth value; (e) searching for an at least second perturbed node along each network path emanating from the node at the center of the graph, wherein the search parameters do not exceed the predetermined search depth value; (f) identifying all at least second perturbed nodes encountered in the search; (g) repeating the search of step (e) for an at least third perturbed node along each path emanating from the at least second perturbed node, wherein the search parameters do not exceed the predetermined search depth value; (h) repeating the identification of step (f) for the at least third perturbed nodes; (i) repeating the search of step (g) and the identification of step (h) for each perturbed node until no more perturbed nodes are found within the predetermined search depth value as measured from each perturbed node; and (j) displaying the graph so as to demarcate all perturbed nodes.

In another embodiment, the methods and systems of the present invention are useful in creating a tool for data analysis, wherein the tool is comprised of (a) loading a reference graph from a reference data source, wherein the paths of the graph are associated with metabolic, regulatory, and signaling pathway network regions; (b) selecting at least a first node and at least a second node to be analyzed; (c) defining a predetermined search depth value; (d) searching for at least one path connecting the first node to the second node, wherein the path length does not exceed the predetermined search depth value; and (e) displaying the graph so as to depict all connecting paths found between each pair of nodes analyzed.

The Nodewalker™ analysis tool resulting from the methods and systems of the present invention allows data to be examined within a biological context. Nodewalker™ provides meaning or context for experimental data, including metabolic, gene expression and proteomic data, by applying the data to a network representation of biological processes.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 3 illustrates that 15 of the 22 components of interest were closely enough related to one another that they fit on a single network graph. The bold, blue outlined compounds (for example, L-asparagine, L-glutamine, L-dopa, GTP, L-serine, and L-ornithine) are the compounds that were measured in the acetaminophen experiment described in Example 1 above. The compounds without a bold blue outline (for example, acetate, L-glutamate, L-cysteine, and L-arginine) were not measured, but are depicted on the graph to provide context for the compounds that were measured. Further graphs (not shown) were generated to illustrate the positions of the remaining 7 components and how they relate to the 15 components depicted in FIG. 3. The graph of FIG. 3, depicting 15 components, was chosen for further investigation because it contained the most components of interest in a single graph.

Figure 5:
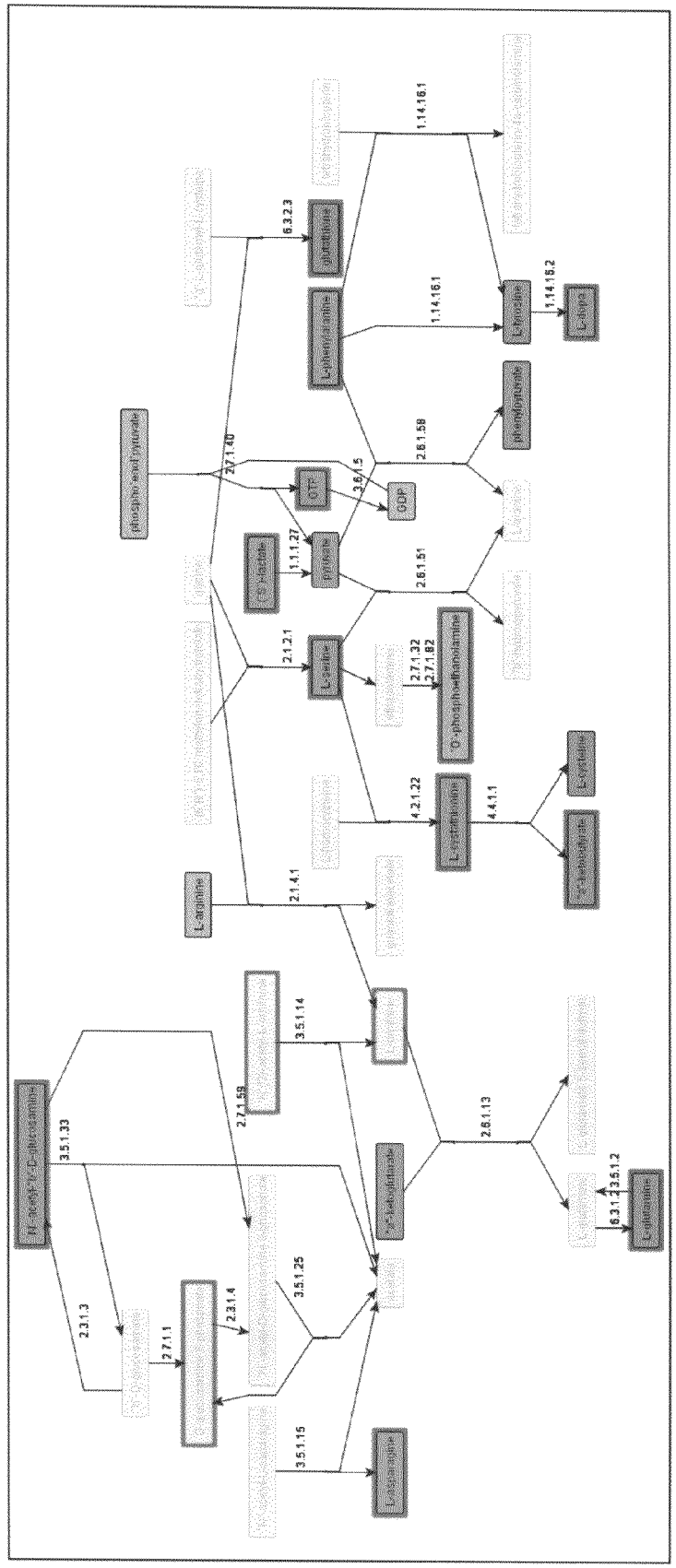
FIG. 5. Illustrated are 15 components of interest, depicted in a network context, with color overlayed to illustrate whether a component was up regulated or down regulated in the acetaminophen experiment of Example 1. A red color in the rectangle illustrating the compound (such as phenylpyruvate and glutathione) indicates that the compound was up regulated during the experiment described in Example 1. A green color in the rectangle illustrating the compound (such as L-serine and L-asparagine) indicates that the compound was down regulated during the experiment described in Example 1. A gray box with typically dark and clear script (such as GDP and L-arginine) indicates that the compound was measured during the experiment and didn't undergo a significant change. A faded gray box with pale script (such as L-alanine and glycine) indicates that the compound was not measured, and is only included to provide network context. It should be noted that not only is the perturbation of the 15 compounds of interest depicted in FIG. 5, but the experimental result from any compound measured and depicted in the network of FIG. 5 is shown. Thus, even though, for example, L-cysteine, L-arginine, and phenylpyruvate were not included in the original list of components of interest, information about them is depicted on the graph of FIG. 5 because of their location in the network.

For the reader's ease, each network component is identified in FIG. 5 by a number (see FIG. 5, bold numbers located above each network component). The identity of each component, along with it's status as "Up Regulated," "Down Regulated," "No Significant Change," or "Not Measured" is provided in the following columns, each number corresponding to the numbered network components of FIG. 5:

| No. | Component Identity | Status |
|---|---|---|
| 1. | 'N'-acetyl-L-asparagine | Not Measured |
| 2. | L-asparagine | Down Regulated |
| 3. | "b"-D-glucosamine | Not Measured |
| 4. | D-glucosamine-6-phosphate | Not Measured |
| 5. | 'N'-acetyl-D-glucosamine-6-phosphate | Not Measured |
| 6. | Acetate | Not Measured |
| 7. | 'N'-acetyl-"b"-D-glucosamine | Down Regulated |
| 8. | "a"-ketoglutarate | Down Regulated |
| 9. | L-glutamate | Not Measured |
| 10. | L-glutamine | Down Regulated |
| 11. | 'N'('2)-acetyl-L-ornithine | Not Measured |
| 12. | L-ornithine | Not Measured |
| 13. | L-glutamate 5-semialdehyde | Not Measured |
| 14. | L-arginine | No Significant Change |

-continued

| No. | Component Identity | Status |
|---|---|---|
| 15. | guanidinoacetate | Not Measured |
| 16. | L-homocysteine | Not Measured |
| 17. | L-cystathionine | Down Regulated |
| 18. | "a"-hetobutyrate | Down Regulated |
| 19. | L-cysteine | Down Regulated |
| 20. | (6'R')-5,10-methylenetetrahydrofolate | Not Measured |
| 21. | L-serine | Down Regulated |
| 22. | Ethanolamine | Not Measured |
| 23. | "o"-phosphoethanolamine | Up Regulated |
| 24. | Glycine | Not Measured |
| 25. | ('S)-lactate | Down Regulated |
| 26. | Pyruvate | Down Regulated |
| 27. | "b"-hydroxypyruvate | Not Measured |
| 28. | L-alanine | Not Measured |
| 29. | Phospho'enol'pyruvate | No Significant Change |
| 30. | GTP | Down Regulated |
| 31. | GDP | No Significant Change |
| 32. | Phenylpyruvate | Up Regulated |
| 33. | L-phenylalanine | Down Regulated |
| 34. | L-tyrosine | Down Regulated |
| 35. | L-dopa | Down Regulated |
| 36. | "a"-L-glutamyl-L-cysteine | Not Measured |
| 37. | glutathione | Up Regulated |
| 38. | tetrahydrobiopterin | Not Measured |
| 39. | trahydrobiopterin-4a-carbinolamine | Not Measured |

Figure 6:
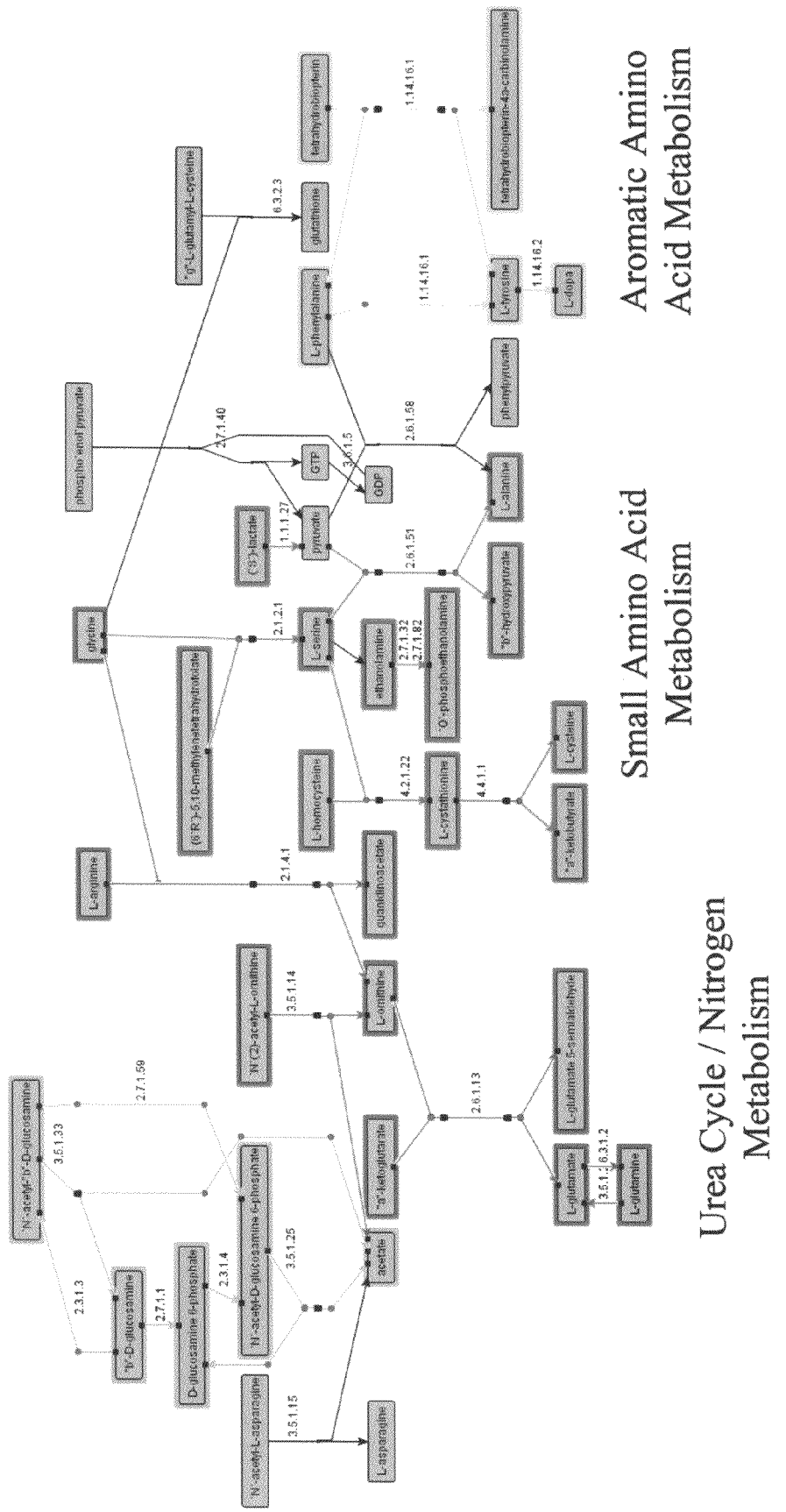

FIG. 6. Illustrated are 15 components of interest, depicted in a network context, with color overlayed to illustrate the biochemical metabolism context of the data. Use of KEGG as the reference data source resulted in identification of four different metabolism pathways affected by the 15 perturbed compounds of interest. The compound rectangles outlined in gold participate in amino sugars metabolism, with corresponding edges/enzymes also in gold. The compound rectangles outlined in pink participate in urea cycle/nitrogen metabolism, with corresponding edges/enzymes also in pink. The compound rectangles outlined in green participate in small amino acid metabolism, with corresponding edges/enzymes also in green. The compound rectangles outlined in bright yellow participate in aromatic amino acid metabolism, with corresponding edges/enzymes also in bright yellow.

DETAILED DESCRIPTION OF THE INVENTION

Definitions

Identifying a "baseline" or control value is essential to biological experimentation and provides, but is not limited to, a mechanism for distinguishing perturbed from unperturbed. A baseline is used in the invention to standardize data to a common or commonly relevant unit of measure. The term "baseline" is herein used to refer to and is interchangeable with "reference" and "control." Baseline populations consist, for example, of data from organisms of a particular group, such as healthy or normal organisms, or organisms diagnosed as having a particular disease state, pathophysiological condition, or other physiological state of interest. An example of the use of a baseline is the expression of data measurements as standard deviations from the corresponding baseline mean.

The term "biochemical pathway" or "pathway" refers to a connected series of biochemical reactions normally occurring in a cell, or more broadly, a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway. Thus, an agent specifically inhibits such a biochemical pathway requiring the expression product of a particular gene if the presence of the agent stops or substantially reduces the completion of the series of steps in that pathway. Such an agent may, but does not necessarily, act directly on the expression product of that particular gene.

"Integrated data" are data related to, or associated with, a unique identifier of a biological sample from which the data were obtained.

For the purpose of this invention, "metabolites" refers to the native small molecules (e.g. non-polymeric compounds) involved in metabolic reactions required for the maintenance, growth, and function of a cell. Enzymes, other proteins, and most peptides are generally not considered to be small molecules and are thus excluded from the definition of metabolite as used herein. Many proteins participate in biochemical reactions with small molecules (e.g. isoprenylation, glycosylation, and the like). The construction and degradation of polypeptides results in either the consumption or generation of small molecules, and thus, the small molecules rather than the proteins are metabolites.

Genetic material (all forms of DNA and RNA) is also excluded as a metabolite based on size and function. The construction and degradation of polynucleotides results in either the consumption or generation of small molecules, and thus, the small molecules rather than the polynucleotides are metabolites. Structural molecules (e.g. glycosaminoglycans and other polymeric units) similarly may be constructed of and/or degraded to small molecules, but do not otherwise participate in metabolic reactions. Thus, structural molecules are excluded from the definition of metabolite as used herein. Polymeric compounds, such as glycogen, are important participants in metabolic reactions as a source of metabolites, but are not chemically defineable (i.e. an input/output to metabolism). Thus, polymeric compounds are excluded from the definition of metabolite as used herein.

Metabolites of xenobiotics (chemical compounds foreign to the body or to living organisms) are neither native, required for maintenance or growth, nor required for normal function of a cell, and thus are not metabolites as used herein. However, it is useful to monitor xenobiotics when observing the effects of a drug therapy program, or in experimentally determining the effects of a compound on an individual. Essential or nutritionally required compounds are not synthesized de novo, (i.e. not native), but are required for the maintenance, growth, or normal function of a cell. Therefore, essential or nutritionally required compounds are metabolites as defined herein.

"Morphology" refers to the form and structure of an organism or any of its parts. Morphology is one way of referring to a phenotype.

"Peak" refers to the readout from any type of spectral analysis or metabolite analysis instrumentation, as is standard in the art, and can represent one or more chemical components. The instrumentation can include, but is not limited to, liquid chromatography (LC), high-pressure liquid chromatography (HPLC), mass spectrometry (MS), hyphenated detection systems such as MS-MS or MS-MS-MS, gas chromatography (GC), liquid chromatography/mass spectroscopy (LC-MS), gas chromatography/mass spectroscopy (GC-MS), Fourier transform-ion cyclotron resonance-mass spectrometry (FT-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS), and matrix-assisted laser desorption/ionization time-of-flight mass spectrometry (MALDI-TOF MS). It is understood that the phrase "mass spectrometry" is used interchangeably with "mass spectroscopy" in this application.

A "perturbed" component is a component of definable interest in an experiment under analysis. For example, perturbation is defined in a statistical way, wherein a perturbed component is a measured experimental component that changed in a statistically significant way. In one example, a perturbed component is any measured experimental component that underwent at least a two-fold up regulation or down regulation. In another example, a perturbed component is any measured experimental component that underwent at least a five-fold up regulation or down regulation. "Perturbed" is defined in any way that is useful in analyzing data.

"Phenotype" refers to the observable physical, morphological, and/or biochemical/metabolic characteristics of an organism, as determined by genetic and/or environmental factors. Histology is the anatomical study of the microscopic physical structure of animal and plant tissues. Thus, histological characteristics are an example of phenotypic data.

Summary statistics are statistical methods applied to data with the intent of summarizing or describing raw unmanipulated data and are familiar to those skilled in the art. In one example, summary statistics can be used to obtain one number, such as an average or a correlation coefficient, to represent an entire data set. Summarization reduces large and complex data sets to a format that is more manageable and meaningful, and multiple summarizations of experimental data may be useful.

Trimming of a graphical depiction of a biological network involves removing unwanted information, or removing information that is uninformative or unnecessary for data analysis. Types of nodes and/or edges that might be trimmed from a graph in the present invention include nodes and/or edges representative of components not measured in the experiment under analysis, or nodes and/or edges that were measured but did not change in a statistically significant way, or nodes and/or edges that are not defined as perturbed. Trimming simplifies and streamlines the information depicted to a user, thus facilitating perception and data analysis. A "raw" graph is graphical representation of a reference graph with data depicted on it, with no editing of the information supplied by the reference data graph source and no editing of the data set under analysis.

"Types of data," as used herein, refer to data derived from different biological indicators. For example, types of data include, but are not limited to, data from DNA, data from RNA, data from proteins, data from metabolites, and data from phenotypic characteristics. Types of data are obtained by any process or technique known in the art; the process or technique used is immaterial in the use of the present invention. However, the process or technique from which the data emanates may affect how the data are integrated. "Disparate data" are comprised of different types of data.

The present invention places biological data in a biological network context and identifies perturbed regions of the network. A biological network is comprised of metabolic, regulatory, and signaling pathways. Methods and systems for identifying perturbed regions in a biological network are useful for numerous biological applications, such as, for example, determining gene function, identifying and validating drug and pesticide targets, identifying and validating drug and pesticide candidate compounds, profiling of drug and pesticide compounds, identifying biomarkers, determining compound site(s) of action, identifying unknown samples, and numerous other applications in the agricultural, pharmaceutical, forensic, and biotechnology industries.

Technologies abound which generate data useful in the study of biological systems. Gene expression profiling, phenotypic analysis, biochemical profiling, proteomics, 3-D protein structural analysis, and protein expression all provide valuable data in a quest for understanding biological systems. Scientific tools, techniques, and technologies, in combination with nucleotide sequence data, single nucleotide polymorphism (SNP) data, scientific literature, clinical chemistry data, and biochemical pathway data, can provide tremendous insight into the workings of complex biological systems when the data are organized, presented and analyzed within a biological context.

In one embodiment of the present invention the data are RNA data (gene expression profiling) and metabolite data (biochemical profiling). In another embodiment of the present invention the data are RNA data and proteomics (protein) data. In still another embodiment of the present invention the data are RNA data, metabolite data, and proteomics data. Further, it is understood by one skilled in the art that data from any biological organism (alive or dead) or part thereof may be incorporated in a Nodewalker™ data analysis. Suitable biological organisms include, but are not limited to, plants, such as *Arabidopsis* (*Arabidopsis thaliana*) and rice, fungal organisms including *Magnaporthe grisea*, *Saccharomyces cerevisiae*, and *Candida albicans*, and mammals, including rodents, rabbits, canines, felines, bovines, equines, porcines, and human and non-human primates.

Suitable sample parts of biological organisms include, but are not limited to, human and animal tissues such as heart muscle, liver, kidney, pancreas, spleen, lung, brain, intestine, stomach, skin, skeletal muscle, uterine muscle, ovary, testicle, prostate, and bone; human and animal fluids such as blood, plasma, serum, urine, mucus, semen, sweat, tears, amniotic fluid, milk; freshly harvested cells such as hepatocytes or spleen cells; immortal cell lines such as the human hepatocyte cell line HepG2, the mouse fibroblast line L929, or other immortal cell lines known to those of skill in the art such as HepG2-C3A, THLE-3, 3T3-L1, MCL-5, H4IIE, HUVEC, L6, C2C12, 3T3-F442A, HIT-T15, C3H10T1/2, T84, and NCI-ADR-Res; human and animal cells grown in culture as three-dimensional culture spheres (e.g. liver spheroids); and plant tissues such as cotyledons, leaves, seeds, open flowers, pistils, senescent flowers, sepals, siliques, and stamens.

Gene expression profiling (GEP) refers to a simultaneous analysis of the expression levels of multiple genes. Traditionally, the expression of individual genes was analyzed by a technique called Northern-blot analysis. In a Northern-blot, RNA is separated on a gel, transferred to a membrane, and a specific gene is identified via hybridization to a radioactive complementary probe, usually made from DNA. A technological improvement in the area of GEP has been the development of small 1-2 cm chips used to concurrently determine expression levels of multiple genes from multiple samples. In a gene chip format, probes for the genes of interest are ordered as an array on a glass slide. After hybridization to appropriate samples, gene expression changes are often visualized with colors overlaid on an image of the chip. The color indicates the gene expression level and the location indicates the specific gene being monitored. Other technologies can be used to obtain the same type of gene information, including high-density array spotting on glass or membranes and quantitative PCR.

Metabolite analysis refers to an analysis of organic, inorganic, and/or bio-molecules (hereinafter collectively referred to as "small molecules") of a cell, cell organelle, tissue and/or organism. It is understood that a small molecule is also referred to as a metabolite. Techniques and methods of the present invention employed to separate and identify small molecules, or metabolites, include but are not limited to: liquid chromatography (LC), high-pressure liquid chromatography (HPLC), mass spectroscopy (MS), gas chromatography (GC), liquid chromatography/mass spectroscopy (LC-MS), gas chromatography/mass spectroscopy (GC-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS), and matrix-assisted laser desorption/ionization time-of-flight mass spectrometry (MALDI-TOF MS).

Metabolite analysis allows the relative amounts of metabolites to be determined in an effort to deduce a biochemical picture of physiology and/or pathophysiology. In one embodiment of the present invention, individual metabolites present in cells are identified and a relative response measured, establishing the presence, relative quantities, patterns, and/or modifications of the metabolites. In a related embodiment of the invention, the metabolites are linked to enzymatic reactions and metabolic pathways. In another embodiment, rather than identifying metabolites, the spectral properties of chemical components in a biological sample are characterized and the presence or absence of the chemical components noted. In a further embodiment of the invention, a metabolic profile is obtained by analyzing a biological sample for its metabolite composition under particular environmental conditions.

Still another type of technology useful in the methods and systems of the present invention is proteomics. Proteins play an important role as structural and functional components of cells and body fluids of living organisms. Proteomics involves the identification of proteins in cells or tissues and their role in physiological function, enabling identification, as well as quantification, of tens of thousands of proteins present in biological samples. Since the total number of proteins expressed in an organism is encoded in its genome, one aim of proteomics is to correlate gene sequences to proteins, and hence to elucidate the function of various genes. The production or suppression of proteins in tissues or cells in response to external stimuli provides an important insight into gene regulation. Proteomic studies can be designed to shed light on the mechanism(s) by which a drug or pesticide acts, as well as provide information regarding various side effects that may be associated with its administration. Relative comparison of protein profiles from normal and diseased tissue may represent proteins that are potential targets for pharmaceutical or agricultural discovery. An understanding of mechanisms occurring at the molecular level is important to designing effective drug therapies, or in determining the function of genes with agricultural importance. In one embodiment of the present invention, proteomics-derived data are contained in a coherent data set to provide an improved understanding of the relationship between genes, proteins, and function.

In the methods and systems of the present invention, data are analyzed in a manner that facilitates the understanding of complex biological systems, a feature that is applicable to many different areas of the life sciences industry. Identification of novel targets for drug, pesticide, and nutriceutical applications is of primary importance. In the pharmaceutical arena alone, it is estimated that existing drugs interact with fewer than 500 biological targets out of an estimated 10,000 potential ones. Based on this estimation, a significant majority of potential drug targets remain undiscovered. In the field of agricultural crop protection, only 20 distinct sites of action for herbicidal compounds have been discovered and reported in the past 60 years, even though estimates of potential herbicide targets exceed this number by two orders of magnitude.

A key component of applying genomics tools to target discovery is the collection of functional information on how genes and gene products impact cells, tissues, organs and their associated healthy and diseased states. While biologically disparate data are being collected and analyzed categorically to address target discovery, the present invention provides a method for placement of data into biologically meaningful groupings or networks to create a data set that describes a condition in greater detail than that achievable through a collective analysis of its individual components.

After new targets for drug, pesticide, and nutriceutical applications are identified, there remains a long and difficult process for the development of an effective product aimed at the identified target. Using the pharmaceutical field as an example, an average of 10,000 lead compounds must be tested in pre-clinical development for every one drug that is ultimately marketed. The methods of the present invention maximize efficiency in bringing targets to product development. In one embodiment of the invention, data from GEP and BCP are analyzed together. In another embodiment, proteomics data and GEP data are analyzed together. In still another embodiment, proteomics data and BCP data are analyzed together. In yet a further embodiment, data from GEP, proteomics, and BCP are analyzed together By using data derived from multiple biological indicators of physiological status, compelling targets can be more thoroughly validated and optimized for greatest effectiveness.

Another area of primary importance in the life sciences industry is the identification of novel lead compounds for use in drug, pesticide, and nutriceutical applications. The methods and systems of the present invention allow biological samples to be analyzed so that the effect of a particular chemical compound on a sample can be understood more thoroughly than was historically possible. Analysis of data in a biological network context allows subtle and complex effects to be observed so that target and lead compound identification, validation and selection are more efficient. The optimization of lead compounds is more efficient as well, as it is possible to optimize the application of the selected leads, and screen-out selected leads based on parameters such as toxicity. The methods and systems of the present invention allow for the development of highly efficacious products while spending as little time and money as possible at a discovery stage.

Discovering and developing new pharmaceutical drugs has become increasingly expensive and challenging. According to the Tufts Center for the Study of Drug Development, the cost of developing a single new drug and bringing it to market (including failures) now exceeds $800 million in the United States. The length of time from the discovery of a candidate to its approval by the FDA has increased from eight years in the 1960s to more than 14 years at the time of this filing. Adverse toxic side effects from drugs result in more than two million hospitalizations each year and more than 100,000 deaths. The methods of the present invention lower the cost of drug discovery, decrease the time to market for new drugs, lower the incidence of adverse toxic side effects, and complement other genomics tools to help researchers better understand the link between cellular or biochemical function, pharmaceutical compounds, toxicity, and disease response. The present invention is also applicable to the discovery and development of new pesticides and nutriceutical products, by lowering the cost of discovery, decreasing the time to market, and lowering the incidence of adverse side effects.

In one embodiment of the present invention, promising pharmaceutical or pesticidal compounds that have failed to reach commercial production due to toxic effects are studied using the methods and systems of the current invention to determine precisely the origin of the toxicity. Armed with information derived using Nodewalker™, it is possible to rescue a failed drug or herbicide compound, or to use Nodewalker™—derived information to select a similar candidate more likely to succeed as a marketable product. The large sums of money invested in the development of failed compounds are not lost and can still result in an effective and marketable product.

Biological markers (biomarkers) are measured characteristics of an organism that correlate with normal or pathogenic biological processes, such as a particular disease state or toxic effect, or lack thereof. As a result, biomarkers are useful for the diagnosis and treatment of disease, and for predictive toxicology. Over the past 200 years, the quantitative chemical analysis of body fluids has steadily evolved to become a critical part of medical diagnosis and patient care (Porter, R. "The Greatest Benefit to Mankind," WW Norton and Company, New York, 1997). Today, clinical laboratories routinely provide data on more than 200 biologically relevant analytes in blood and urine that can signal serious illness and monitor well-being. However, it has become increasingly clear that single markers (e.g. glucose), like single genes, do not provide adequate information about complex diseases, and that composite biomarkers are much more likely to be of prognostic value.

There is currently renewed interest in the identification of biomarkers for staging clinical diseases, providing insights into mechanisms of drug action and predicting toxicity. Recent examples of the use of biomarkers for the prediction of disease and toxicity include U.S. Pat. No. 6,540,691, "Breath test for the detection of various diseases;" U.S. Pat. No. 6,537,744, "Use of biomarkers in saliva to evaluate the toxicity of agents and the function of tissues in both biomedical and environmental applications;" U.S. Pat. No. 6,500,633, "Method of detecting carcinomas;" and U.S. Pat. No. 6,465,195, "Predictive diagnosis for Alzheimer's disease." Hepatic toxicity is of particular importance, as it accounts for approximately 80% of toxicological failures in pre-clinical studies of potential pharmaceutical agents. In addition, liver toxicity is the major reason for failure of new chemical entities in clinical trials and the major reason existing drugs are pulled from the market.

The present invention provides methods and systems that support the identification and use of biomarkers for disease and/or toxicity, disease staging, target identification/validation, and monitoring of drug efficacy/toxicity. Biomarkers are particularly useful as a non-invasive and early predictor of hepatic toxicity.

To meet the overall challenge of analyzing large, complex data sets, the present invention places data in a biological context and recognizes patterns within a biological network. Nodewalker™ automatically identifies perturbed metabolic, regulatory, and signaling pathway network regions in biological data. Individual Nodewalker™ network components are identified as nodes, which are representative of either a metabolic compound or a protein. When nodes are depicted within a network, graph edges are used to link nodes and therefore the graph edges represent interactions between nodes. In one example, the edges represent biochemical enzymes, which are encoded by genes. A search depth value is predetermined and serves as a guide as to how far along a network path, or through how many node interactions, a search proceeds before stopping. Only relationships or interactions that fall within the parameters of the predetermined search depth value will be graphically depicted.

Experimental design and conditions include any factors that can be used to stratify data. The experimental design and conditions recorded may include, but are not limited to, organism species; organism type within a species (such as sex (male or female); age; race; body type (obese, thin, tall, short); behaviors such as smoking or exercising; presence or absence of disease; mutant type; or other factors contributing to a patient profile); sample type (tissue or fluids such as blood or urine); treatment type (drug or pesticide compound, mode of administration, length of time administered and amount administered); time point of sample harvest; or any clinical characteristic. Suitable sample parts of biological organisms include, but are not limited to, human and animal tissues such as heart muscle, liver, kidney, pancreas, spleen, lung, brain, intestine, stomach, skin, skeletal muscle, uterine muscle, ovary, testicle, prostate, and bone; human and animal fluids such as blood, plasma, serum, saliva, urine, mucus, semen, vaginal fluid, sweat, tears, amniotic fluid, and milk; freshly harvested cells such as hepatocytes or spleen cells; immortal cell lines such as the human hepatocyte cell line HepG2, the mouse fibroblast line L929, or other immortal cell lines known to those of skill in the art such as HepG2-C3A, THLE-3, 3T3-L1, MCL-5, H4IIE, HUVEC, L6, C2C12, 3T3-F442A, HIT-T15, C3H10T1/2, T84, and NCI-ADR-Res; human and animal cells grown in culture as three-dimensional culture spheres (e.g. liver spheroids); cultured fungi; and plant tissues such as cotyledons, leaves, seeds, open flowers, pistils, senescent flowers, sepals, siliques, and stamens.

Data measurements may include, but are not limited to, gene expression profiling, phenotypic analysis, metabolite analysis, proteomics, histological analysis, tissue feature analysis, 3-D protein structural analysis, and protein expression analysis. Other types of information useful in the methods of the invention include nucleotide sequence data, single nucleotide polymorphism (SNP) data, scientific literature, clinical chemistry data, and biochemical pathway data, all of which can provide tremendous insight into the workings of complex biological systems.

Gene expression profiling (GEP) refers to a simultaneous analysis of the expression levels of multiple genes. Traditionally, the expression of individual genes was analyzed by a technique called Northern-blot analysis. In a Northern-blot, RNA is separated on a gel, transferred to a membrane, and a specific gene is identified via hybridization to a radioactive complementary probe, usually made from DNA. A technological improvement in the area of GEP has been the development of small 1-2 cm chips used to concurrently determine expression levels of multiple genes from multiple samples. In a gene chip format, probes for the genes of interest are ordered as an array on a glass slide. After hybridization to appropriate samples, gene expression changes are often visualized with colors overlaid on an image of the chip. The color indicates the gene expression level and the location indicates the specific gene being monitored. Other technologies can be used to obtain the same type of gene information, including high-density array spotting on glass or membranes and quantitative reverse transcription and PCR.

Phenotype refers to observable physical or biochemical/metabolic characteristics of an organism, as determined by genetic and environmental factors. For example, in an *Arabidopsis thaliana* plant model system, a phenotype can be described by using distinctly defined attributes such as, but not limited to, number of: abnormal seeds, cotyledons, normal seeds, open flowers, pistils per flower, senescent flowers, sepals per flower, siliques, and stamens. Perturbation of a biological system is often indicated by a phenotypic trait. In humans, a perturbed biological system may result in symptoms of disease such as chest pain, signs such as elevated blood pressure, or observable physical traits such as those exhibited by individuals afflicted with Trisomy 21. A normal phenotype is useful as a baseline value against which a physiological status can be measured.

Medical history, examination, and testing techniques are well known to medical practitioners and data derived from the same can be used in practicing the methods and systems of the present invention. For example, in cases where a practitioner is examining a patient to determine the likelihood, existence, or extent of coronary heart disease (CHD), phenotypic traits observed or identified in a clinical setting include, but are not limited to, risk factors such as blood pressure, cigarette smoking, total cholesterol (TC), low density lipoprotein cholesterol (LDL-C), high density lipoprotein cholesterol (HDL-C), and diabetes. P. G. McGovern et al., 334 NEW ENG. J. MED. 884-890 (1996). Additional phenotypic characteristics such as body weight, family history of CHD, hormone replacement therapy, and left ventricular hypertrophy are also useful in determining CHD risk. It is common in the medical arts to scale or score a patient's condition based on a set of phenotypic signs and symptoms. For example, predictive models have been described based on blood pressure, cholesterol, and LDL-C categories as identified by the National Cholesterol Education Program and the Joint National Committee on Detection, Evaluation, and Treatment of High Blood Pressure. P. W. F. Wilson et al., 97 CIRCULATION 1837-1847 (1998) (incorporated herein by reference). Furthermore, predictive outcome models have also been described for patients undergoing coronary artery bypass grafting surgery and percutaneous transluminal coronary angioplasty.

Medical scoring of phenotypic traits is applicable to the assessment of patient well-being pre- and post-therapeutic intervention. For example, Short-Form 36 (SF-36) is gaining acceptance as a generic health outcome assessment form. SF-36 validates health outcomes with eight indices of health and well-being including general health (GH), physical function (PF), role function due to physical limitations (RP), role function due to emotional limitations (RE), social function (SF), mental health (MH), bodily pain (BP), and vitality and energy (VE). Each health object is scored on a 0 to 100 basis with higher scores representing better function or less pain. Other scoring or ranking schemas for identifying and quantifying physiologic and pathophysiologic (phenotypic) states (traits) include, not are not limited, the following: ATP III Metabolic Syndrome Criteria; Criteria for One Year Mortality Prognosis in Alcoholic Liver Disease; APACHE II Scoring System and Mortality Estimates (Acute Physiology and Chronic Health disease Classification System II); APACHE II Scoring System by Diagnosis; Apgar Score; Arrhythmogenic Right Ventricular Dysplasia Diagnostic Criteria; Arterial Blood Gas Interpretation; Autoimmune Hepatitis Diagnostic Criteria; Cardiac Risk Index in Noncardiac Surgery (L. Goldman et al., 297 NEW ENG. J. MED. 20 (1977)); Cardiac Risk Index in Noncardiac Surgery (A. S. Detsky et al., 1 J. GEN. INT. MED. 211-219 (1986)); Child Turcotte Pugh Grading of Liver Disease Severity; Chronic Fatigue Syndrome Diagnostic Criteria; Community Acquired Pneumonia Severity Scale; DVT Probability Score System; Ehlers-Danlos Syndrome IV (Vascular Type) Diagnostic Criteria; Epworth Sleepiness Scale (ESS); Framingham Coronary Risk Prediction (P. W. F. Wilson et al., 97 CIRCULATION 1837-1847 (1998)); Gail Model for 5 Year Risk of Breast Cancer (M. H. Gail et al., 91 J. NAT'L CANCER INST. 1829-1846 (1999); Geriatric Depression Scale; Glasgow Coma Scale; Gurd's Diagnostic Criteria for Fat Embolism Syndrome; Hepatitis Discriminant Function for Prednisolone Treatment in Severe Alcoholic Hepatitis; Irritable Bowel Syndrome Diagnostic Criteria (A. P. Manning et al., 2 BRIT. MED. J. 653-654 (1978)); Jones Criteria for Diagnosis of Rheumatic Fever; Kawasaki Disease Diagnostic Criteria; M. I. Criteria for Likelihood in Chest Pain with LBBB; Mini-Mental Status Examination; Multiple Myeloma Diagnostic Criteria; Myelodysplastic Syndrome International Prognostic Scoring System; Nonbiliary Cirrhosis Prognostic Criteria for One Year Survival; Obesity Management Guidelines (National Institutes of Health/NHLBI); Perioperative Cardiac Evaluation (NHLBI); Polycythemia Vera Diagnostic Criteria; Prostatism Symptom Score; Ranson Criteria for Acute Pancreatitis; Renal Artery Stenosis Prediction Rule; Rheumatoid Arthritis Criteria (American Rheumatism Association); Romhilt-Estes Criteria for Left Ventricular Hypertrophy; Smoking Cessation and Intervention (NHLBI); Sore Throat (Pharyngitis) Evaluation and Treatment Criteria; Suggested Management of Patients with Raised Lipid Levels (NHLBI); Systemic Lupus Erythematosis American Rheumatism Association 11 Criteria; Thyroid Disease Screening for Females More Than 50 Years Old (NHLBI); and Vector and Scalar Electrocardiography.

Still other phenotypic traits could be observed or identified by x-ray; cardiac and vascular angiography; electrocardiography; blood pressure (BP) examination; pulse; weight and height; ideal body weight or BMI; retinal examination; thyroid examination; carotid bruits; neck vein examination; congestive heart failure (CHF) signs; palpable intercostal pulses; cardiovascular examination traits including, but not limited to, S4 gallop, tachycardia, bradycardia, heart sounds, aortic insufficiency, murmur, and echocardiography; abdominal examination; genitourinary examination; peripheral vascular disease examination; neurologic examination; and skin examination. In addition to standard x-ray technologies, numerous imaging techniques are also useful in observing and identifying phenotypic traits including, but not limited to, ultrasound, magnetic resonance imaging (MRI), positron emission tomography (PET), single photon emission computed tomography (SPECT), x-ray transmission, x-ray computed tomography (X-ray CT), ultrasound electrical impedance tomography (EIT), electrical source imaging (ESI), magnetic source imaging, (MSI) laser optical imaging.

Metabolite or biochemical analysis (also referred to as biochemical profiling or BCP) refers to an analysis of organic, inorganic, and/or bio-molecules (hereinafter collectively referred to as "small molecules") of a cell, cell organelle, tissue and/or organism. It is understood that a small molecule is also referred to as a metabolite. Techniques and methods of the present invention employed to separate and identify small molecules, or metabolites, include but are not limited to: liquid chromatography (LC), high-pressure liquid chromatography (HPLC), mass spectroscopy (MS), gas chromatography (GC), liquid chromatography/mass spectroscopy (LC-MS), gas chromatography/mass spectroscopy (GC-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS), and matrix-assisted laser desorption/ionization time-of-flight mass spectrometry (MALDI-TOF MS).

Metabolite or biochemical analysis allows relative amounts of metabolites to be determined in an effort to deduce a biochemical picture of physiology and/or pathophysiology. In one embodiment of the present invention, individual metabolites present in cells are identified and a relative response measured, establishing the presence, relative quantities, patterns, and/or modifications of the metabolites. In a related embodiment of the invention, the metabolites are related to enzymatic reactions and metabolic pathways. In another embodiment, rather than identifying metabolites, the spectral properties of chemical components in a biological sample are characterized and the presence or absence of the chemical components noted. In a further embodiment of the invention, a metabolic profile is obtained by analyzing a biological sample for metabolite composition under particular environmental conditions.

The methods and systems of the present invention are also useful in conjunction with data derived from histology studies. Histology is the anatomical study of the microscopic structure of animal and plant tissues. Histological analyses include recordation of traits directly observable and recordation of findings from image analysis. In one embodiment, the histological images are in an electronic format. In another embodiment, tissue feature analysis techniques are used in the acquisition of histological phenotypic data. Tissue feature analysis refers to quantitative tissue image analysis of structural features in tissue elements using digital microscopy to generate data that objectively describes tissue phenotype, with potential for detection of subtle changes that are undetectable to the human eye. One example of tissue feature analysis is described in Kriete et al., 4 Genome Biology R32.1-0.9 (2003).

Reference information sources useful in the present invention include, but are not limited to, KEGG (Kyoto Encyclopedia of Genes and Genomes, Institute for Chemical Research, Kyoto University, Japan), BRENDA (The Comprehensive Enzyme Information System, Institute of Biochemistry, University of Cologne, Germany), Expert Protein Analysis System (ExPASy), or any other information source that provides a biological context for data analysis, including a proprietary data source. The biological context may include a biochemical pathways context, which may include substrates, products, and enzymes (all metabolites) and the genes that encode the metabolites. In another embodiment, a signal transduction context or a protein-binding (protein-protein interactions) context, such as cell surface binding, protein kinase reactions (signal transduction), cytokine binding (signal transduction), or antibody binding, is provided. In another embodiment, a cellular organelle context, such as a mitochondrial context, a cellular context, a tissue context, an organ context, an organ system context, or an entire organism context, is provided. In another embodiment, a chromosomal context, such as genes or metabolites represented on a chromosome map of a particular organism, is provided. In another embodiment, an image context is provided, such as a CAT (or CT) scan, an MRI, a histology image such as a section of an organ or tissue, a depiction of a human body, a depiction of a human tissue, organ, or organ system, a depiction of a leaf, a root, a stem, a flower, a seed, an entire plant, or any image of an organism or any part thereof. In yet another embodiment, a protein structure or model context is provided, such as the structure of an enzyme complex, on which genes are superimposed. In another embodiment, a context of global architecture of genetic interactions on protein networks is provided (O. Ozier et al., 21 NATURE BIOTECH., 490-491 (2003)). It is understood by those skilled in the art that any information source that is electronically recorded may be used in the methods and systems of the invention.

To support the methods and systems of the present invention, proper technical infrastructure must be available. Appropriate computer hardware is supplied, for example, by the Sun Microsystems' E420 workgroup server (Sun Microsystems, Inc., Santa Clara, Calif.). Appropriate operating systems include, but are not limited to, Solaris (Sun Microsystems, Inc., Santa Clara, Calif.), Windows (Microsoft Corp., Redmond, Wash.), or Linux (Red Hat, Inc., Raleigh, N.C.). Appropriate software applications include, but are not limited to, relational databases such as Oracle 9.0.1 (9i) (Oracle Corp., Redwood Shores, Calif.), DB2 Universal Database V8.1 (IBM Corp., Armonk, N.Y.), or SQL Server 2000 (Microsoft Corp., Redmond, Wash.), software for metabolic, regulatory, and signaling pathway network representation such as Cytoscape (open community software resulting from a collaboration between Institute for Systems Biology (Dr. Benno Schwikowski), Memorial Sloan-Kettering Cancer Center (Drs. Chris Sander and Gary Bader) and University of California at San Diego (Dr. Trey Ideker)) or GenMap (Open Biosystems, Huntsville, Ala.) and software for statistical analyses, such as packages available from SAS (SAS Institute, Inc., Cary, N.C.) or SPSS, Inc. (SPSS, Inc., Chicago, Ill.). In one embodiment, the server is the E420 workgroup server (Sun Microsystems, Inc., Santa Clara, Calif.), the operating system is Solaris (Sun Microsystems, Inc., Santa Clara, Calif.), the software for pathway network representation is Cytoscape v1.1.1, the database software is Oracle 9.0.1 (9i) (Oracle Corp., Redwood Shores, Calif.), and statistical software is from SAS (SAS Institute, Inc., Cary, N.C.).

The present inventors have recognized that the massive amounts of biological data now available call for technological developments that support analyses of different types of data collectively and in a biologically relevant context. The invention presented herein is an analysis tool that facilitates recognition and identification of trends and relationships within complex data.

The methods and systems of the present invention provide a tool that enables a user to query data without any preconceived knowledge of the relationships between network components. Thus, the methods and systems of the present invention provide information for determining whether perturbation is generalized across the biological network (e.g., a system-wide, nonspecific toxicity), or is localized to a particular network region (e.g., affecting only a single biochemical element, function, or pathway, such as biosynthesis of a particular amino acid).

Accordingly, the present invention provides methods and systems for analyzing biological data, comprising (a) loading a reference graph from a reference data source, wherein the paths of the graph are associated with metabolic, regulatory, and signaling pathway network regions; (b) selecting at least one perturbed node to be analyzed; (c) placing the perturbed node to be analyzed at the center of a graph; (d) defining a predetermined search depth value; (e) searching for an at least second perturbed node along each network path emanating from the node at the center of the graph, wherein the search parameters do not exceed the predetermined search depth value; (f) identifying all at least second perturbed nodes encountered in the search; (g) repeating the search of step (e) for an at least third perturbed node along each path emanating from the at least second perturbed node, wherein the search parameters do not exceed the predetermined search depth value; (h) repeating the identification of step (f) for the at least third perturbed nodes; (i) repeating the search of step (g) and the identification of step (h) for each perturbed node until no more perturbed nodes are found within the predetermined search depth value as measured from each perturbed node; and (j) displaying the graph so as to demarcate all perturbed nodes.

In another embodiment, the present invention provides methods and systems for analyzing biological data, comprising (a) loading a reference graph from a reference data source, wherein the paths of the graph are associated with metabolic, regulatory, and signaling pathway network regions; (b) selecting at least one perturbed node to be analyzed; (c) placing the perturbed node to be analyzed at the center of a graph; (d) defining a predetermined search depth value; (e) searching for an at least second perturbed node along each network path emanating from the node at the center of the graph, wherein the search parameters do not exceed the predetermined search depth value; (f) identifying all at least second perturbed nodes encountered in the search; (g) repeating the search of step (e) for an at least third perturbed node along each path emanating from the at least second perturbed node, wherein the search parameters do not exceed the predetermined search depth value; (h) repeating the identification of step (f) for the at least third perturbed nodes; (i) repeating the search of step (g) and the identification of step (h) for each perturbed node until no more perturbed nodes are found within the predetermined search depth value as measured from each perturbed node; (j) displaying the graph so as to demarcate all perturbed nodes; and (k) trimming the graph so that all network paths depicted represent only measured nodes.

In a further embodiment, the present invention provides methods and systems for analyzing biological data, comprising (a) loading a reference graph from a reference data source, wherein the paths of the graph are associated with metabolic, regulatory, and signaling pathway network regions; (b) selecting at least one perturbed node to be analyzed; (c) placing the perturbed node to be analyzed at the center of a graph; (d) defining a predetermined search depth value; (e) searching for an at least second perturbed node along each network path emanating from the node at the center of the graph, wherein the search parameters do not exceed the predetermined search depth value; (f) identifying all at least second perturbed nodes encountered in the search; (g) repeating the search of step (e) for an at least third perturbed node along each path emanating from the at least second perturbed node, wherein the search parameters do not exceed the predetermined search depth value; (h) repeating the identification of step (f) for the at least third perturbed nodes; (i) repeating the search of step (g) and the identification of step (h) for each perturbed node until no more perturbed nodes are found within the predetermined search depth value as measured from each perturbed node; (j) displaying the graph so as to demarcate all perturbed nodes; and (k) trimming the graph so that all network paths depicted end at a perturbed node.

In another embodiment, the present invention provides methods and systems for analyzing biological data, comprising (a) loading a reference graph from a reference data source, wherein the paths of the graph are associated with metabolic, regulatory, and signaling pathway network regions; (b) selecting at least one perturbed node to be analyzed; (c) placing the perturbed node to be analyzed at the center of a graph; (d) defining a predetermined search depth value; (e) searching for an at least second perturbed node along each network path emanating from the node at the center of the graph, wherein the search parameters do not exceed the predetermined search depth value; (f) identifying all at least second perturbed nodes encountered in the search; (g) repeating the search of step (e) for an at least third perturbed node along each path emanating from the at least second perturbed node, wherein the search parameters do not exceed the predetermined search depth value; (h) repeating the identification of step (f) for the at least third perturbed nodes; (i) repeating the search of step (g) and the identification of step (h) for each perturbed node until no more perturbed nodes are found within the predetermined search depth value as measured from each perturbed node; (j) displaying the graph so as to demarcate all perturbed nodes; and (k) trimming the graph so that all network paths depicted represent only measured nodes and all network paths depicted end at a perturbed node.

In still another embodiment, the present invention provides methods and systems for analyzing biological data, comprising (a) loading a reference graph from a reference data source, wherein the paths of the graph are associated with metabolic, regulatory, and signaling pathway network regions; (b) selecting at least one perturbed node to be analyzed; (c) placing the perturbed node to be analyzed at the center of a graph; (d) defining a predetermined search depth value; (e) searching for an at least second perturbed node along each network path emanating from the node at the center of the graph, wherein the search parameters do not exceed the predetermined search depth value; (f) identifying all at least second perturbed nodes encountered in the search; (g) repeating the search of step (e) for an at least third perturbed node along each path emanating from the at least second perturbed node, wherein the search parameters do not exceed the predetermined search depth value; (h) repeating the identification of step (f) for the at least third perturbed nodes; (i) repeating the search of step (g) and the identification of step (h) for each perturbed node until no more perturbed nodes are found within the predetermined search depth value as measured from each perturbed node; and (j) displaying both a raw version and a trimmed version of the graph between which a user can toggle.

The methods and systems of the present invention provide a tool that enables a user to query data by providing a list of components of interest, wherein the components of interest share a commonality. Thus, the methods and systems of the present invention provide information for determining how the components of interest on the list are related in a biological network context.

In yet another embodiment, the present invention provides methods and systems for analyzing biological data, comprising (a) loading a reference graph from a reference data source, wherein the paths of the graph are associated with metabolic, regulatory, and signaling pathway network regions; (b) selecting at least a first node and at least a second node to be analyzed; (c) defining a predetermined search depth value; (d) searching for at least one path connecting the first node to the second node, wherein the path length does not exceed the predetermined search depth value; and (e) displaying the graph so as to depict all connecting paths found between each pair of nodes analyzed.

In another embodiment, the present invention provides methods and systems for analyzing biological data, comprising (a) loading a reference graph from a reference data source, wherein the paths of the graph are associated with metabolic, regulatory, and signaling pathway network regions; (b) selecting at least a first node and at least a second node to be analyzed; (c) defining a predetermined search depth value; (d) searching for at least one path connecting the first node to the second node, wherein the path length does not exceed the predetermined search depth value; (e) displaying the graph so as to demarcate all connecting paths found between each pair of nodes analyzed; and (f) trimming the graph so that all network paths depicted represent only measured or perturbed nodes.

In a further embodiment, the present invention provides methods and systems for analyzing biological data, comprising (a) loading a reference graph from a reference data source, wherein the paths of the graph are associated with metabolic, regulatory, and signaling pathway network regions; (b) selecting at least a first node and at least a second node to be analyzed; (c) defining a predetermined search depth value; (d) searching for at least one path connecting the first node to the second node, wherein the path length does not exceed the predetermined search depth value; (e) displaying the graph so as to demarcate all connecting paths found between each pair of nodes analyzed; and (f) trimming the graph so that only the connecting path of shortest length between each pair of nodes is depicted.

In still another embodiment, the present invention provides methods and systems for analyzing biological data, comprising (a) loading a reference graph from a reference data source, wherein the paths of the graph are associated with metabolic, regulatory, and signaling pathway network regions; (b) selecting at least a first node and at least a second node to be analyzed; (c) defining a predetermined search depth value; (d) searching for at least one path connecting the first node to the second node, wherein the path length does not exceed the predetermined search depth value; and (e) displaying both a raw version and a trimmed version of the graph between which a user can toggle.

In further embodiments, all of the above embodiments are practiced by replacing "node" (used to represent a compound or protein) with "edge" (used to represent an enzyme encoded by a gene). It is understood by those of ordinary skill in the art that not all possible embodiments of Nodewalker™ are listed here and, accordingly, additional embodiments of the Nodewalker™ analysis tool fall under the scope of the present invention.

EXPERIMENTAL

Example 1

Acetaminophen-Induced Liver Toxicity Study Design and Data Acquisition

An acetaminophen-induced liver toxicity study was performed as follows. Male Fischer 344 rats were administered a single dose of acetaminophen (APAP) at 0, 50, 150, 1500 or 2000 mg/kg p.o. (6 rats per group). The 150 mg/kg dose is equivalent to a low overdose level in humans (~10 g) and 1500 mg/kg is a low toxic dose in rats. The rats were sacrificed at 6, 18, 24, and 48 hr post dosing. Livers of the rats were processed for biochemical profiling, histopathology and gene expression analysis. For the 0, 50 and 1500 mg/kg dose groups, rat urine was collected at −24-0, 0-6, 6-24, and 24-48 hr relative to dosing. Similarly, rat serum was collected at 48 hr for the 0, 50 and 1500 mg/kg groups.

Sample Preparation

Rat tissue was prepared for LC-MS analysis as follows. Rat liver tissue samples were frozen upon collection. A slice of each frozen sample was placed into a mortar, covered with liquid nitrogen, and ground with a pestle. 100 mg of ground sample was placed in a cryovial, extraction fluid and beads were added, and the sample was further ground and then centrifuged. The supernatant was transferred to a clean cryovial, centrifuged again, and then transferred to a well of a 96-well plate.

Rat biofluids were prepared for LC-MS analysis as follows. Rat urine and serum samples were vortexed. An aliquot of 500 µl was transferred to a clean cryovial and centrifuged. The supernatant was transferred to a clean cryovial and centrifuged again. The supernatant was transferred to another clean cryovial and diluted 4:1 with extraction solvent. An aliquot of 100 µl was transferred to a well of a 96-well plate.

LC-MS Analysis

LC-MS analysis of the rat tissue and biofluid samples was performed on an Applied Biosystems Mariner liquid chromatograph coupled with a time of flight mass spectrometer (LC-TOF). The mass resolution for the mass spectrometer employed in this experiment was 0.200 amu. One LC was employed with a splitter that allowed for the eluent to be delivered to two TOF MS instruments, one operating in positive ionization mode, the other in negative ionization mode. Compounds detected by LC-MS with an electrospray ion source were cataloged based on retention times and mass-to-charge ratio (m/z) of the ions characteristic of each peak. Mass spectrometric data were collected from 80-900 amu. Raw LC-MS data were processed using the commercially available software TARGETDB (Thru-Put Systems, Inc., Orlando, Fla.).

RNA Isolation

Upon necropsy, liver tissue from left lateral lobe is cubed (0.5 cm or smaller) and stored in RNALATER (Ambion, Austin, Tex.) overnight at 4+/−3° C. then transferred to −20+/−10° C. until RNA isolation (within 60 days). RNA is isolated from approximately 130-150 mg tissue using RNEASY midi spin columns (Qiagen, Valencia, Calif.) according to the manufacturer's protocol. The RNA is concentrated using Millipore Microcon centrifugal filter devices (Billerica, Mass.).

RNA Labeling/Microarray Hybridization

One µg total RNA from either an individual rat or a pooled sample is amplified and labeled with a fluorophore (either Cy3 or Cy5) using Agilent Technologies' Low RNA Input Linear Amplification Labeling (Palo Alto, Calif.) following the manufacturer's protocol. The resulting fluorescently labeled cRNA is tested on a Nanodrop ND-100 spectrophotometer (Rockland, Del.) and an Agilent Bioanalyzer (Palo Alto, Calif.) to ensure proper quantity and quality. Equal amounts (750 ng) of Cy3-labeled cRNA from an individual rat and Cy5-labeled cRNA from the corresponding pooled control are hybridized to an Agilent Rat Oligo Array (Palo Alto, Calif.). In a second hybridization, the fluorophores used to label each sample are reversed. Therefore, two hybridizations are performed for each individual rat examined in this study.

Example 2

Figure 1:
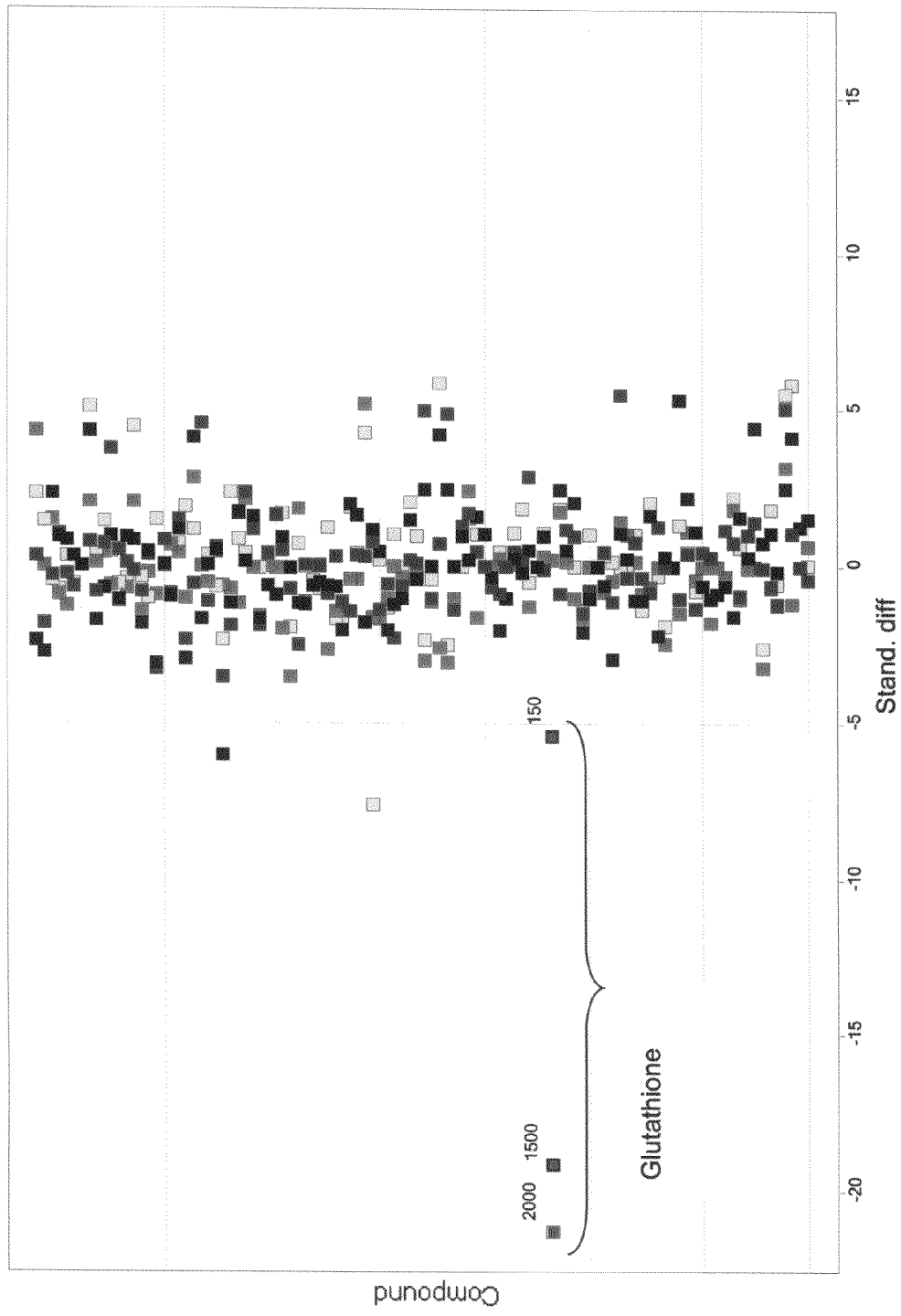
FIG. 1. Overview of metabolite data of rat liver biochemical profiling data collected for a study of acetaminophen-induced liver toxicity. Rats administered a single dose of acetaminophen (APAP) at 150, 1500 or 2000 mg/kg p.o. were sacrificed at 6 hr post dosing (6 rats per group). Livers of the rats were processed for biochemical profiling data and the standard difference of each data point (x-axis) is plotted against the identified compound (y-axis).
Figure 2:
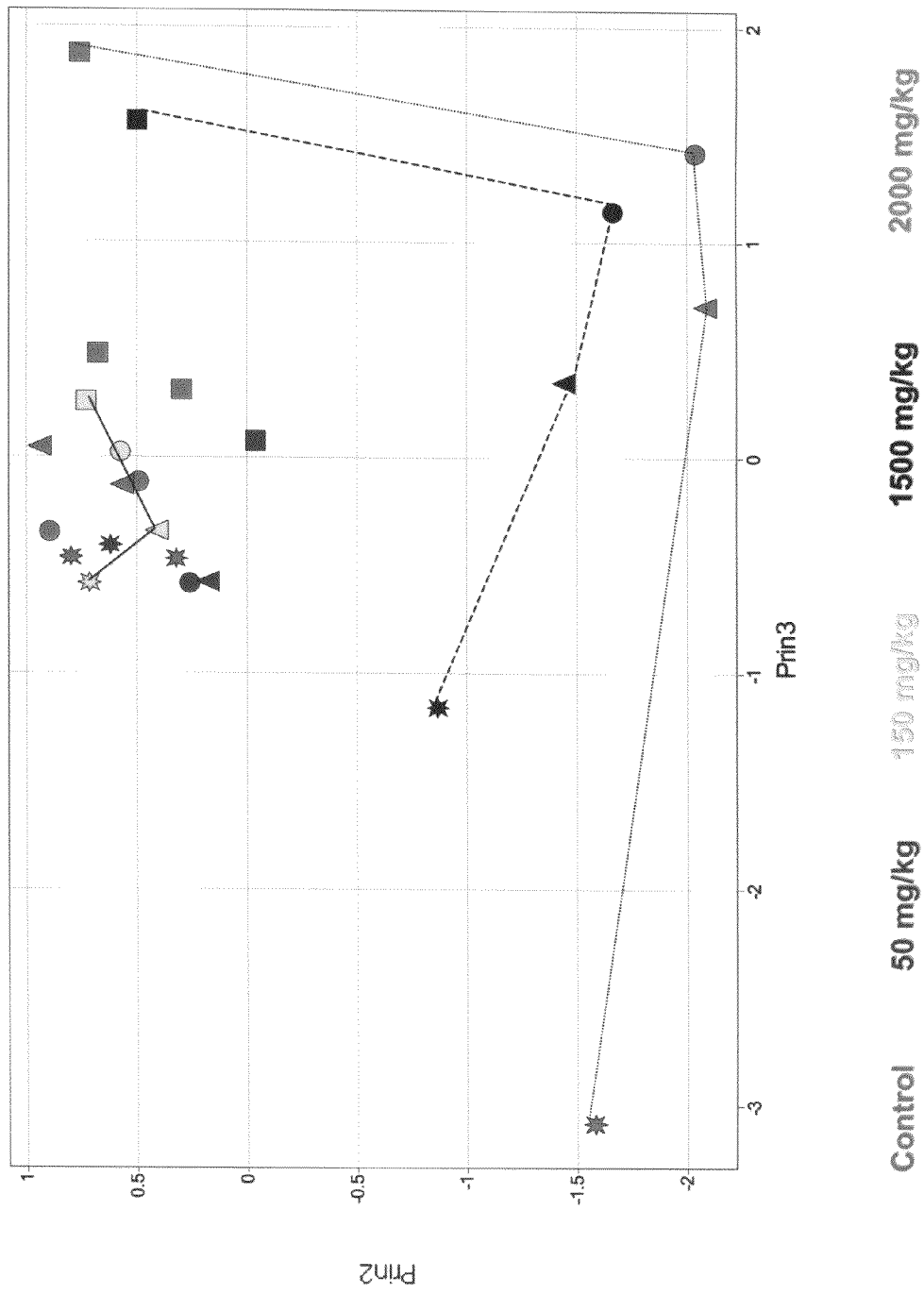
FIG. 2. Principal component analysis (PCA) of rat liver biochemical profiling data collected for a study of acetaminophen-induced liver toxicity. Rats administered a single dose of acetaminophen (APAP) at 150, 1500 or 2000 mg/kg p.o. were sacrificed at 6, 18, 24, or 48 hr post dosing (6 rats per group). Livers of the rats were processed for biochemical profiling data and the third principal component (x-axis) is plotted against the second principal component (y-axis) for each of the 6, 18, 24 and 48 hr time points at 150 mg/kg (yellow), 1500 mg/kg (black), and 2000 mg/kg (green) concentrations of acetaminophen. Each data point represents the average for six animals.

Data Analysis Methods: Locating a Subset of Most Interest that Corresponds to an Observed Trend A targeted list of relative responses for peaks and peaks annotated as known compounds was produced from the LC/MS data for the rat liver samples described in Example 1 and is illustrated in FIG. 1. The resulting biochemical profiling data was subjected to Principal Component Analysis (PCA), showing trends over both dose and time (see FIG. 2). The third principal component (x-axis) is plotted against the second principal component (y-axis) for each of the 6, 18, 24 and 48 hr time points for acetaminophen doses 150 mg/kg (yellow), 1500 mg/kg (black), and 2000 mg/kg (green). Each data point represents the average for six animals.

Mathematical models of the trends observed in the PCA plot were developed. Two trends were observed in the PCA plot. Trend 1 is a trend of increasing distance from control as the dose increases at any given time point. Trend 2 is a trend of change from one time point to the next that is in the same direction and of increasing magnitude as dose increases. Each of the relative response peaks in the liver biochemical profiling dataset was tested for adherence to the mathematical models to locate the subset of peaks that followed the observed trends. The peaks that adhered to the models were identified as the subset of most interest for further analysis of acetaminophen-induced liver changes. To further investigate the mode of action of acetaminophen, the known compounds in the identified subset were further analyzed using the methods and systems of the present invention.

In another example, the same type of analysis as that discussed above in Example 2 is applied using gene data or protein data.

Example 3

Figure 3:
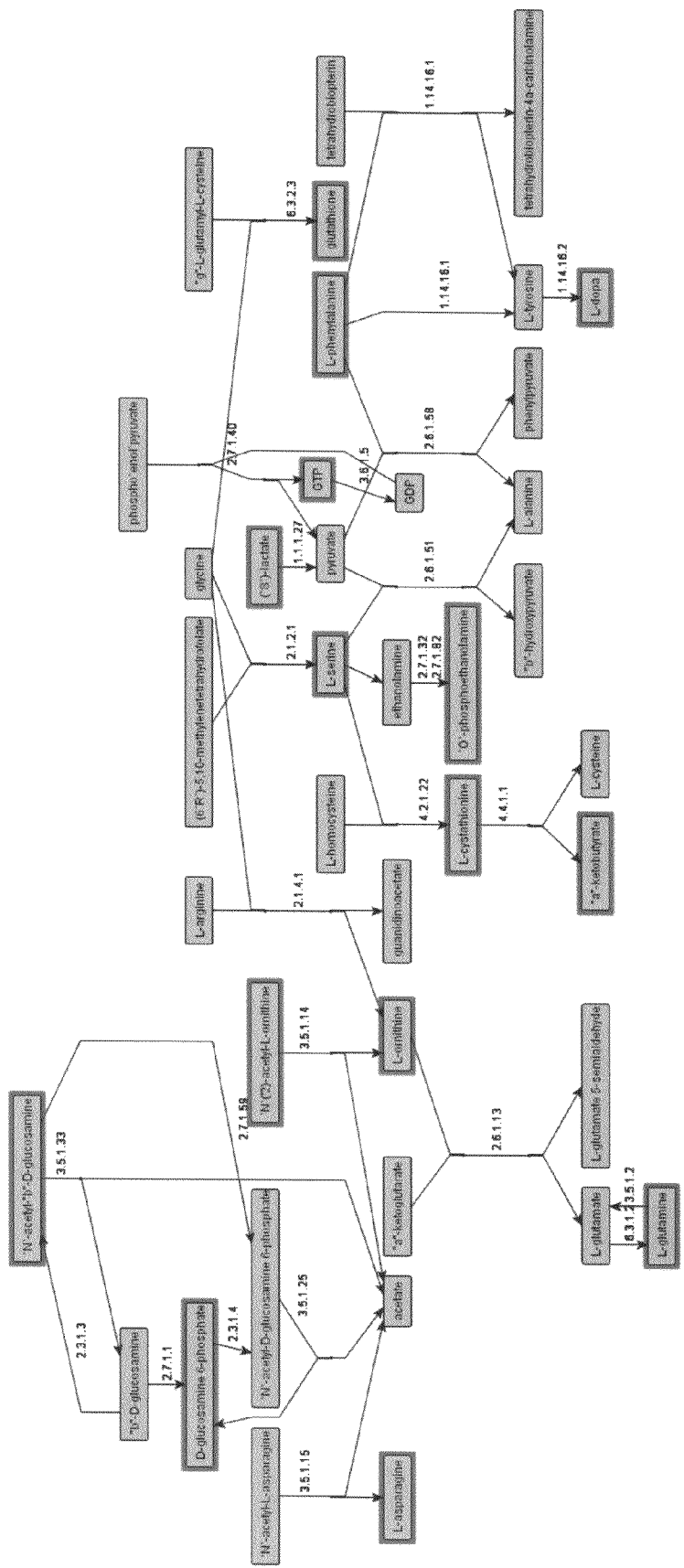
FIG. 3. A reference graph was loaded from a reference data source (KEGG), wherein the paths of the graph were associated with metabolic, regulatory, and signaling pathway network. Components of interest were defined as peaks measured in the acetaminophen experiment and found to follow at least one of two mathematical trends for statistically significant change within the experiment, as discussed in Example 2. 22 biochemical compounds were identified as components of interest. The components of interest were placed as nodes at the center of a graph, fitting as many components of interest into a single graph as space allowed.

Data Analysis Methods: Locating the Subset of Most Interest in a Network Context The data from the acetaminophen experiment of Example 1 were analyzed as follows. A reference graph was loaded from a reference data source (KEGG), wherein the paths of the graph were associated with metabolic, regulatory, and signaling pathway network. Components of interest were defined as peaks measured in the acetaminophen experiment and found to follow at least one of two mathematical trends for statistically significant change within the experiment, as discussed in Example 2 above. 22 biochemical compounds were identified as components of interest and were further analyzed by the methods and systems of the invention. The components of interest were placed as nodes at the center of a graph, fitting as many components of interest into a single graph as space allowed. FIG. 3 illustrates that 15 of the 22 components of interest were closely enough related to one another that they fit on a single network graph. The bold, blue outlined compounds (for example, L-asparagine, L-glutamine, L-dopa, GTP, L-serine, and L-ornithine) are the compounds that were measured in the acetaminophen experiment described in Example 1 above. The compounds without a bold blue outline (for example, acetate, L-glutamate, L-cysteine, and L-arginine) were not measured, but are depicted on the graph to provide context for the compounds that were measured. Further graphs were generated to illustrate the positions of the remaining 7 components and how they relate to the 15 components depicted in FIG. 3. The graph depicting 15 components (FIG. 3) was chosen for further investigation because it contained the most components of interest in a single graph.

Figure 4:
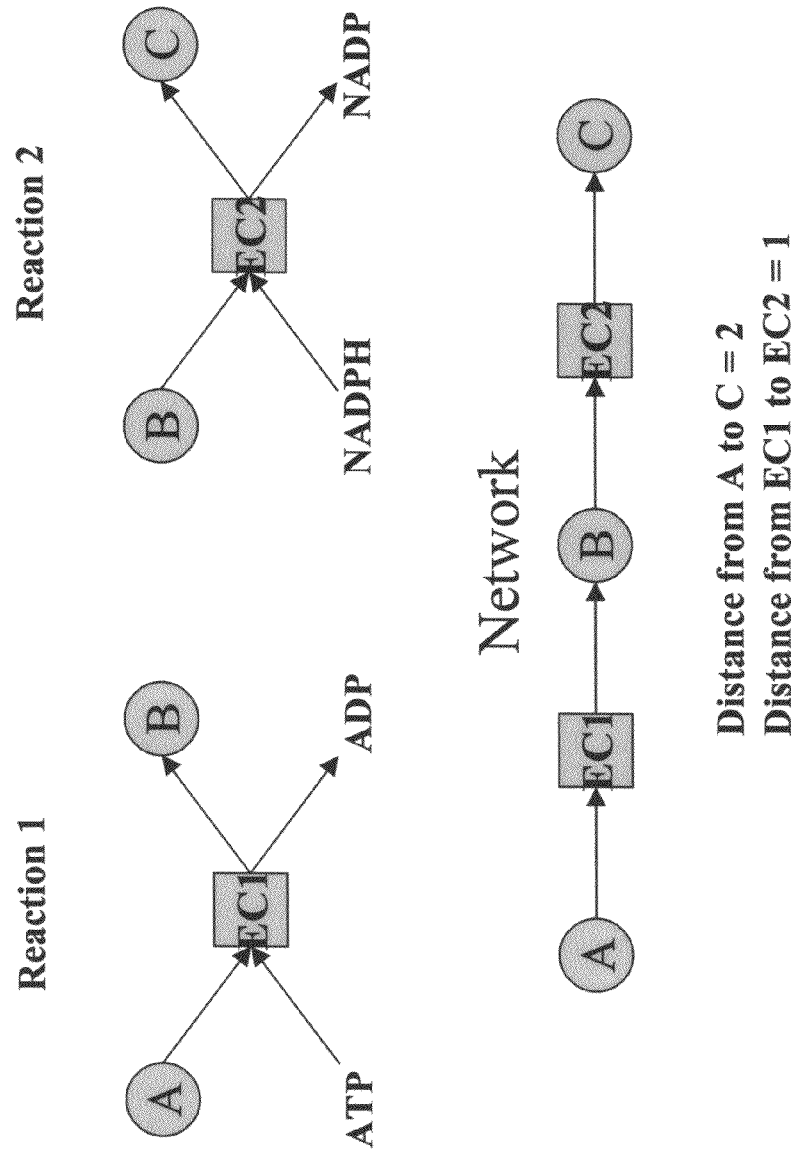
FIG. 4. Biochemical reactions, such as Reaction 1 and Reaction 2, are typically depicted as substrate(s) (circle A in Reaction 1 and circle B in Reaction 2) and product(s) (circle B in Reaction 1 and circle C in Reaction 2) connected by an enzyme (square EC1 in Reaction 1 and square EC2 in Reaction 1)). ATP, ADP, NADPH, and NADP are representative of different cofactors that may be required to complete a particular biochemical reaction. Depictions of biochemical reactions have typically been presented or depicted as a single reaction (such as Reaction 1 or Reaction 2) represented separately from any other reaction. In a network depiction of biochemical reactions, single biochemical reactions are linked together as shown in the Network depiction at the bottom of FIG. 4, thereby removing repetition (such as circle B's representation in both Reaction 1 (as a product) and Reaction 2 (as a substrate)) and illustrating distance relationships between network components. A search distance is computed as illustrated in the Network depiction at the bottom of FIG. 4, with a distance of 1 assigned between components A and B, B and C, and EC1 and EC2, and a distance of 2 between A and C.

A predetermined search depth value was defined for creation of the graph in FIG. 3. The search value was defined according to distances between biochemical reactions. As shown in FIG. 4, biochemical reactions, such as Reaction 1 and Reaction 2, are typically depicted as substrate(s) (circle A in Reaction 1 and circle B in Reaction 2) and product(s) (circle B in Reaction 1 and circle C in Reaction 2) connected by an enzyme (square EC1 in Reaction 1 and square EC2 in Reaction 1)). ATP, ADP, NADPH, and NADP are representative of different cofactors that may be required to complete a particular biochemical reaction. Depictions of biochemical reactions have typically been presented or depicted as a single reaction (such as Reaction 1 or Reaction 2) represented separately from any other reaction. In a network depiction of biochemical reactions, single biochemical reactions are linked together as shown in the Network depiction at the bottom of FIG. 4, thereby removing repetition (such as circle B's representation in both Reaction 1 (as a product) and Reaction 2 (as a substrate)) and illustrating distance relationships between network components. A search distance for FIG. 3 was computed as illustrated in the Network depiction at the bottom of FIG. 4, with a distance of 1 assigned between components A and B, B and C, and EC1 and EC2. A search depth value of 3 was used in analyzing the results depicted in FIG. 3.

Thus, in one embodiment, the methods and systems of the current invention operate such that, given a current node, "A," and a reaction "A+B→C+D," "A's" neighbors are the nodes on the opposite site of the equation arrow. These neighbors are considered to be a distance value of one away from "A." Nodes on the same side of the reaction arrow are not considered to be neighbors. Thus, "A's" neighbors are "C" and "D," not "B." When the search steps to node "C," its neighbors are nodes that are products of any reaction that "C" is a substrate in.

One factor which complicates the measure of distance in biochemical reactions and networks is the presence of cofactors and ubiquitous compounds, such as water and ATP, which are present in hundreds or even thousands of reactions throughout the network. For example, ATP is a substrate in 414 reactions in KEGG and a product in 17 reactions. ADP is a substrate in 18 reactions in KEGG and a product in 298 reactions. The presence of these compounds during analysis can distort network pattern recognition. Thus, relevance is assigned to the reference graph components. Water is always considered irrelevant and is not depicted in results. Some compounds, such as GTP, are relevant in some cases and not relevant in others. A scientist assigns relevance to components as appropriate for each analysis. Assignment of relevance is exceedingly helpful, as it reduces the amount of uninformative data depicted in the final analysis graphs generated by the methods and systems of the present invention, thereby increasing the simplicity and value of the information depicted.

In another example, the same type of analysis as that discussed above in Example 3 is applied using gene data or protein data.

Example 4

Data Analysis Methods: Perturbation in the Subset of Most Interest in a Network Context Using the methods and systems of the present invention, another graph was generated depicting the 15 components of interest, from Example 3 above, that were closely related enough to fit on a single graph. FIG. 5 illustrates the 15 components of interest, depicted in a network context, with color overlayed to illustrate whether the component was up regulated or down regulated in the acetaminophen experiment. A red color in the rectangle illustrating the compound (such as phenylpyruvate and glutathione) indicates that the compound was up regulated during the experiment described in Example 1. A green color in the rectangle illustrating the compound (such as L-serine and L-asparagine) indicates that the compound was down regulated during the experiment described in Example 1. A gray box with typically dark and clear script (such as GDP and L-arginine) indicates that the compound was measured during the experiment and didn't undergo a significant change. A faded gray box with pale script (such as L-alanine and glycine) indicates that the compound was not measured, and is only included to provide network context. It should be noted that not only is the perturbation of the 15 compounds of interest depicted in FIG. 5, but the experimental result from any compound measured and depicted in the network of FIG. 5 is shown. Thus, even though, for example, L-cysteine, L-arginine, and phenylpyruvate were not included in the original list of components of interest, information about them is depicted on the graph of FIG. 5 because of their location in the network. This is a very powerful utility offered by Nodewalker™, as now the results of all components measured and found in the network location depicted on the graph are considered during analysis, leading to a better system-wide understanding of what happens during an acetaminophen overdose.

In addition to providing information about biochemical compounds, their relationship in a network context, and whether the compounds changed significantly during the experiment, FIG. 5 illustrates how a second data type is integrated into the graph generated by the methods and systems of the current invention. Gene expression data is overlayed on the graph on the graph edges linking the nodes. The gene expression data was obtained from the acetaminophen experiment described in Example 1, and those genes encoding enzymes pertinent to the biochemical reactions depicted on the graph in FIG. 5 are shown. The color coding system is the same as for the compounds, wherein a red arrow indicates up regulation of the gene, and a green arrow indicates down regulation of the gene. This feature of the invention disclosed herein allows a user to incorporate gene expression data and biochemical compound data into one network context, thus facilitating analysis of data and recognition of relationships within data.

In another example, the same type of analysis as that discussed above in Example 4 is applied using gene data or protein data.

Example 5

Data Analysis Methods: the Subset of Most Interest in a KEGG Network Context

The methods and systems of the current invention are applied to generation of another graph, depicted in FIG. 6, depicting the 15 components of interest from Example 3 above. FIG. 6 illustrates the 15 components of interest, depicted in a network context, with color overlayed to illustrate the biochemical metabolism context of the data. As shown in FIG. 6, using KEGG as the reference data source, four different metabolism pathways were identified in the graph of the 15 components of interest. The compound rectangles outlined in gold participate in amino sugars metabolism, with corresponding edges/enzymes also in gold. The compound rectangles outlined in pink participate in urea cycle/nitrogen metabolism, with corresponding edges/enzymes also in pink. The compound rectangles outlined in green participate in small amino acid metabolism, with corresponding edges/enzymes also in green. The compound rectangles outlined in bright yellow participate in aromatic amino acid metabolism, with corresponding edges/enzymes also in bright yellow.

In another example, using KEGG as the reference data source, metabolism pathways are identified by matching enzyme/gene perturbations with KEGG information. Thus, in FIG. 5, enzymes observed to change significantly during the experiment of Example 1, such as Enzyme Class (E. C.) number 2.7.1.32 and E. C. number 2.7.1.82, are matched to the KEGG reference data to identify perturbed regions of biochemical metabolism and used to generated a graph such as the one depicted in FIG. 6.

In still another example, using KEGG as the reference data source, metabolism pathways are identified by matching protein perturbations with KEGG information. Thus, in FIG. 5, proteins observed to change significantly during the experiment of Example 1 are matched to the KEGG reference data to identify perturbed regions of biochemical metabolism and used to generated a graph such as the one depicted in FIG. 6.

Example 6

Data Analysis Methods: Locating Perturbed components in a Network Context

The data from the acetaminophen experiment of Example 1 are analyzed as follows. A reference graph is loaded from a reference data source (KEGG), wherein the paths of the graph were associated with metabolic, regulatory, and signaling pathway network. Components of interest are defined as peaks or genes measured in the acetaminophen experiment and found to change in a statistically significant way within the experiment of Example 1. The components of interest are placed as nodes or edges at the center of a graph, fitting as many components of interest into a single graph as space allows. A predetermined search depth value, such as 3, is defined and utilized as shown in FIG. 4.

The methods and systems of the current invention proceed along the network in all directions from, for example, each perturbed node to the predetermined search depth value. If no more perturbed nodes are encountered, that pathway of the graph is terminated. If a perturbed node is encountered, the Nodewalker™ tool begins to search for further perturbed nodes within the predetermined search depth value. Searching continues until all paths are terminated.

The graph is displayed in various depictions. In one example, the raw graph is displayed, with no information experiment edited out or trimmed away. In another example, the graph is displayed so that all pathways terminate at a perturbed node. In another example, the graph is displayed so that all pathways terminate at a perturbed node and only nodes that were measured are depicted. In another example, a user can toggle between a raw graphical depiction and a trimmed graphical depiction, wherein all pathways terminate at a perturbed node and/or only measured nodes are depicted.

In another embodiment, the methods and systems of the present invention are applied using gene data and, subsequently, graph edges. The methods and systems of the current invention proceed along the network in all directions from, for example, each perturbed edge to the predetermined search depth value. If no more perturbed edges are encountered, that pathway of the graph is terminated. If a perturbed edge is encountered, the Nodewalker™ tool begins to search for further perturbed edges within the predetermined search depth value. Searching continues until all paths are terminated.

In another example, the same type of analysis as that discussed above is applied using protein data.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A computational method for analyzing biological data to identify components that are related to a perturbation, the method comprising:
   a) loading a reference graph from a reference data source, wherein the paths of the graph are associated with metabolic, regulatory, or signaling pathway network regions;
   b) associating experimental data collected from an experiment relating to at least one of a metabolic pathway, a regulatory pathway, and a signaling pathway with representative features of the graph, wherein each feature corresponds to a single node of the graph or a single edge of the graph;
   c) selecting at least one perturbed feature to be analyzed, wherein a perturbed feature comprises a feature having a plurality of experimental data values associated with that feature, wherein the experimental data values associated with, that feature have changed in a statistically significant way relative to a baseline value associated with that feature and wherein the experimental data values associated with that feature exhibit a mathematical trend with respect to an independent variable of the experimental data;
   d) defining a predetermined search depth value;
   e) searching for an at least second perturbed feature along each network path emanating from the selected at least one perturbed feature, wherein the search parameters do not exceed the predetermined search depth value;
   f) identifying all at least second perturbed features encountered in the search;
   g) repeating the search of step (e) for an at least third perturbed feature along each path emanating from the at least second perturbed feature, wherein the search parameters do not exceed the predetermined search depth value;
   h) repeating the identification of step (f) for the at least third perturbed features;
   i) repeating the search of step (g) and the identification of step (h) for each perturbed feature until no more perturbed features are found within the predetermined search depth value as measured from each perturbed feature; and
   j) displaying to a user the graph so as to demarcate all perturbed features of the graph to distinguish them from unperturbed features of the graph, wherein all of steps a) through j) inclusive are performed by a suitably-programmed computer.

2. The method of claim 1, wherein the graph is trimmed so that all network paths depicted represent only measured features.

3. The method of claim 1, wherein the graph is trimmed so that each network path depicted in the graph ends at a perturbed feature.

4. The method of claim 1, wherein a user can toggle between a raw version of the graph and a trimmed version of the graph.

5. The method of claim 1, wherein the reference data source is KEGG.

6. The method of claim 1, wherein the independent variable comprises time.

7. The method of claim 1, wherein the independent variable comprises a dosage of an agent that is applied to a sample from which the experimental data is derived but is not applied to a sample from which the baseline value is derived.

8. A computational method for analyzing biological data to identify components that are related to a perturbation, the method comprising:
   a) loading a reference graph from a reference data source, wherein the paths of the graph are associated with metabolic, regulatory, or signaling pathway network regions;
   b) associating experimental data collected from an experiment relating to at least one of a metabolic pathway, a regulatory pathway, and a signaling pathway with representative features of the graph, wherein each feature corresponds to a single node of the graph or a single edge of the graph;
   c) selecting at least a first perturbed feature and at least a second perturbed feature to be analyzed, wherein a perturbed feature comprises a feature having a plurality of experimental data values associated with that feature, wherein the experimental data values associated with that feature have changed in a statistically significant way relative to a baseline value associated with that feature and wherein the experimental values associated with that feature exhibit a mathematical trend with respect to an independent variable of the experimental data;
   d) searching for at least one path connecting the first feature to the second feature; and
   e) displaying to a user the graph so as to demarcate all connecting paths found between each pair of features analyzed to distinguish them from paths that do not connect any pair of features,
   wherein all of steps a) through e) inclusive are performed by a suitably-programmed computer.

9. The method of claim 8, wherein the graph is trimmed so that all network paths depicted represent only features with which experimental data has been associated.

10. The method of claim 8, wherein the graph is trimmed so that only the connecting path of shortest length between each pair of features is depicted.

11. The method of claim 8, wherein a user can toggle between a raw version of the graph and a trimmed version of the graph.

12. The method of claim 8, wherein the reference data source is KEGG.

13. The method of claim 8, comprising, in response to failing to find at least one path connecting the first feature to the second feature, providing in a user-readable form an indication that a path may exist between the first and second features on the reference graph.

14. The method of claim 13 wherein searching for at least one path connecting the first feature to the second feature comprises searching within a path length that does not exceed a predetermined search depth value.

15. The method of claim 13 wherein providing in a user-readable form an indication that a path may exist between the first and second features on the reference graph comprises providing an indication that a previously unidentified path may exist between the first and second features.

16. The method of claim 8 wherein searching for at least one path connecting the first feature to the second feature comprises defining a predetermined search depth value and wherein the path length does not exceed the predetermined search depth value.

17. The method of claim 8, wherein the independent variable comprises time.

18. The method of claim 8, wherein the independent variable comprises a dosage of an agent that is applied to a sample from which the experimental data is derived but is not applied to a sample from which the baseline value is derived.

* * * * *